United States Patent
Löser et al.

(10) Patent No.: US 9,468,784 B2
(45) Date of Patent: Oct. 18, 2016

(54) RESPIRATOR AND WALL MOUNT FOR A RESPIRATOR

(71) Applicant: Dräger Medical GmbH, Lübeck (DE)

(72) Inventors: Judith Löser, Lübeck (DE); Tobias Otte, Lübeck (DE); Uwe Reimann, Lübeck (DE); Thomas Rossen, Lübeck (DE)

(73) Assignee: DRÄGERWERK AG & Co. KGaA, Lübeck (DE)

( * ) Notice: Subject to any disclaimer, the term of this patent is extended or adjusted under 35 U.S.C. 154(b) by 335 days.

(21) Appl. No.: 13/716,627

(22) Filed: Dec. 17, 2012

(65) Prior Publication Data
US 2013/0247912 A1    Sep. 26, 2013

(30) Foreign Application Priority Data
Mar. 20, 2012 (DE) .................. 10 2012 005 668

(51) Int. Cl.
*A62B 25/00* (2006.01)
*A62B 7/02* (2006.01)
(Continued)

(52) U.S. Cl.
CPC .............. *A62B 25/00* (2013.01); *A61M 16/10* (2013.01); *A62B 7/02* (2013.01); *A61M 16/0051* (2013.01); *A61M 2016/0027* (2013.01); *A61M 2016/0036* (2013.01); *A61M 2202/0208* (2013.01); *A61M 2205/502* (2013.01); *A61M 2205/584* (2013.01); *A61M 2205/8206* (2013.01); *A61M 2209/086* (2013.01); *A61M 2230/432* (2013.01)

(58) Field of Classification Search
CPC ... A62B 7/02; A62B 25/00; A61M 2209/08; A61M 2209/082; A61M 2209/084; A61M 2209/088; A61M 16/00; A61M 2205/6045; A62C 13/78; B62B 1/264; B62B 4/104; B62B 5/0016; B62B 2202/02; B62B 2202/022
USPC ............ 128/200.24, 200.29, 202.12, 202.28, 128/204.18, 204.21, 205.22, 205.26; 600/21, 22; 248/311.2; 5/626
See application file for complete search history.

(56) References Cited

U.S. PATENT DOCUMENTS

| | | | | |
|---|---|---|---|---|
| 3,733,008 A | * | 5/1973 | Churchill | A62B 25/00 128/202.26 |
| 4,182,322 A | * | 1/1980 | Miller | A61F 5/05883 5/637 |
| 4,586,687 A | * | 5/1986 | Ziaylek, Jr. | A62B 9/04 169/51 |

(Continued)

FOREIGN PATENT DOCUMENTS

| | | |
|---|---|---|
| CN | 2245991 Y | 1/1997 |
| DE | 73 36 747 U | 11/1974 |

(Continued)

*Primary Examiner* — Tan-Uyen (Jackie) T Ho
*Assistant Examiner* — Joseph D Boecker
(74) *Attorney, Agent, or Firm* — McGlew and Tuttle, P.C

(57) ABSTRACT

A respirator (1) and a mount for a respirator are provided including a mounting device for a cylinder (2), preferably an oxygen cylinder. The mounting device forms an upper housing half (4) and a lower housing half (3) of the respirator (1) and includes at least one grip (6), which makes transportation of the respirator (1) possible. The upper housing half (4) and lower housing half (3) are provided with a connection mechanism (5), which connects the upper housing half (4) and the lower housing half (3).

19 Claims, 13 Drawing Sheets

(51) Int. Cl.
*A61M 16/10* (2006.01)
*A61M 16/00* (2006.01)

(56) References Cited

U.S. PATENT DOCUMENTS

| | | | | |
|---|---|---|---|---|
| 5,820,207 A * | 10/1998 | Wang | ............ | A47D 1/002 297/135 |
| 6,042,130 A * | 3/2000 | Souza | ............ | B62B 1/12 280/79.5 |
| 6,386,559 B1 * | 5/2002 | Souza | ............ | B60R 7/043 280/47.26 |
| 6,415,786 B1 * | 7/2002 | Kolbe | ............ | A62B 25/00 128/200.24 |
| 6,883,766 B1 * | 4/2005 | Ziaylek | ............ | A62B 9/04 248/154 |
| 7,394,387 B2 * | 7/2008 | Noonchester | ............ | A62B 3/00 2/44 |
| 2002/0063193 A1 * | 5/2002 | Field | ............ | A62B 25/00 248/313 |
| 2003/0115671 A1 * | 6/2003 | Smeed | ............ | A61G 1/04 5/503.1 |
| 2004/0040091 A1 * | 3/2004 | Hampe | ............ | A61G 7/05 5/503.1 |
| 2004/0108429 A1 * | 6/2004 | Field | ............ | A62C 13/78 248/311.2 |
| 2005/0072426 A1 * | 4/2005 | Deane | ............ | A61M 16/10 128/204.26 |
| 2006/0086356 A1 * | 4/2006 | Nahavandi | ............ | A61M 16/10 128/200.24 |
| 2006/0174408 A1 * | 8/2006 | Flannery | ............ | A47C 21/08 5/426 |
| 2008/0035807 A1 * | 2/2008 | Bevirt | ............ | F16M 11/40 248/163.1 |
| 2008/0190947 A1 | 8/2008 | Bourgraf | | |
| 2008/0257928 A1 * | 10/2008 | Lowry | ............ | A45F 3/04 224/638 |
| 2009/0320207 A1 * | 12/2009 | Noonchester | ............ | A62B 3/00 5/626 |
| 2011/0272975 A1 * | 11/2011 | Hogg | ............ | B60R 11/00 297/188.04 |
| 2012/0091692 A1 * | 4/2012 | Moore | ............ | B60D 1/01 280/504 |
| 2012/0175855 A1 * | 7/2012 | Lautzenhiser | ............ | A61G 5/1037 280/47.371 |
| 2012/0204868 A1 * | 8/2012 | Allan | ............ | A62B 25/00 128/201.23 |

FOREIGN PATENT DOCUMENTS

| | | |
|---|---|---|
| DE | 102 39 467 A1 | 3/2004 |
| DE | 203 17 702 U1 | 3/2004 |
| DE | 10 2007 016 410 A1 | 10/2007 |

* cited by examiner

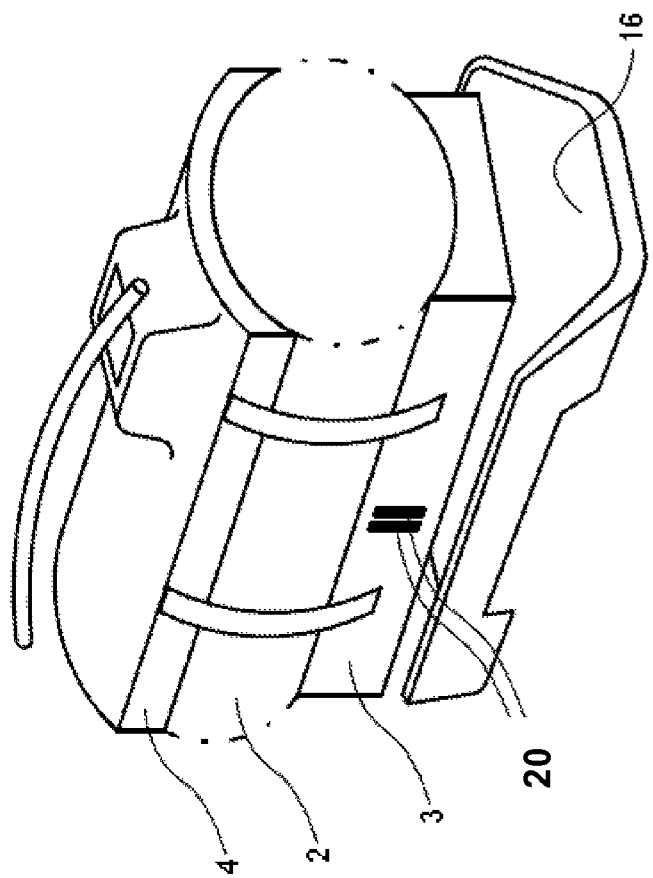
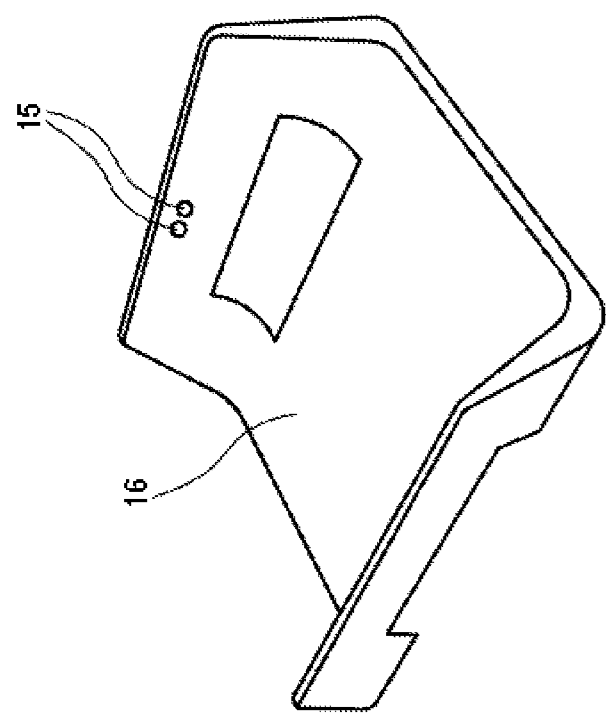
Fig. 12b
Fig. 12a

RESPIRATOR AND WALL MOUNT FOR A RESPIRATOR

CROSS REFERENCE TO RELATED APPLICATIONS

This application claims the benefit of priority under 35 U.S.C. §119 of German Patent Application 10 2012 005 668.0 filed Mar. 20, 2012, the entire contents of which are incorporated herein by reference.

FIELD OF THE INVENTION

The present invention pertains to a respirator and a mount for a respirator.

BACKGROUND OF THE INVENTION

Respiration of a patient with an emergency respirator becomes necessary, in general, when disturbances develop in spontaneous respiration. The persons to be respirated are usually in a building, such as private homes or public buildings, but, of course, also outside buildings, e.g., in an automobile on a road or on sidewalks. An emergency may be triggered, e.g., by a sudden myocardial infarction or an automobile accident or an accident at work. In any case, the patient must be treated on the site of the event and transported into an adequate medical facility for further treatment. This comprises first aid on site, transportation to a hospital, or even from one hospital to another hospital or within a hospital building.

Numerous emergency respirators are known in the state of the art. Emergency respirators are typically arranged on the wall of an ambulance, rescue helicopter or in a building, e.g., a hospital or physician's office, and can be brought to the site of the accident or to the person requiring respiration. For transportation, the devices can be mounted on a carrying system alone or together with their accessories, e.g., oxygen cylinder, breathing tubes, filters. Besides the breathing tube, the oxygen cylinder belongs to the necessary equipment that must always be carried along, because patients with disturbances of the cardiovascular system are always supplied with oxygen.

To make direct supply of the patient on the site of use possible, the supply devices must be transportable. However, the environment in which the patient is located may vary greatly. For example, the patient may be in a very crowded or poorly accessible environment, e.g., in an apartment in an old building, which can be reached only via narrow stairwells. Persons may also be trapped in a wrecked automobile after an automobile accident, or there is a situation in which accidents occur during mountain hikes and the patient is in a rather remote area. However, even if accessibility is guaranteed, the devices must be brought to the patient from the ambulance or the storage site and brought to the destination together with the patient after the first aid, in which case uneven road surfaces, slippery ground, high steps, narrow bends make rescue difficult.

During the transportation of the supply devices outside the ambulance, these devices are either carried or suspended, for example, at the patient stretcher with fastening means or simply placed beside the patient on the stretcher. Special mounts are also frequently provided to make it possible to fasten the fastening means on rails or on a stretcher. The emergency respirators can then be fastened in an ambulance to a wall mount directly or by means of the carrying system. Mounted in the wall mount, the devices are ready to operate.

Device-specific wall mounts are available for emergency respirators. The mounts are metal constructions, which are screwed flatly on the wall and to which the respective emergency respirators are fastened by means of rails and a snap mechanism. The snap mechanism is preferably located at the upper end and the rails at the lower end of the mount.

To arrange the carrying system on a mount, the carrying system is introduced at first from the top into a lower rail and then pressed against an upper end of the mount, so that the carrying system will then snap automatically into the snap mechanism and is held in the mount. To separate the carrying system from the mount, a human operator must hold the grip of the carrying system with one hand and release a lever of the snap mechanism with his other hand, so that the system can then be lifted obliquely upward and out of the rail or mount.

A certain arrangement in space of the emergency respirator, carrying system and accessories, including the oxygen cylinder, is determined by the mode of construction of the emergency respirator, carrying system and wall mount. The grip of the carrying system is in an upper position in this arrangement, the emergency respirator is located under it with user interfaces, such as a display and setting elements pointing forward or obliquely upward, and the pockets for flexible tubes and other accessories under it. The oxygen cylinder is in the lower position.

The respirators, which are prepared for transportation with an oxygen cylinder to the site of use, are mounted in a separate rack. The dimensioning of the rack is determined by the dimensions for a type of cylinder. Installation of a cylinder of a larger volume is often possible with difficulty only, if at all. The replacement of attached parts on the frame of the rack requires a tool and skilled manipulation with the hands. Especially disturbing is the rather non-ergonomic replacement of cylinders, which must be frequently performed. In case of some products, the carrying rack must be removed for this from its mount, clamped connections must be opened and the cylinder must be removed from the rack.

The carrying rack determines the dimensions and presets the possibility of carrying and fastening. Thus, a narrow and higher construction will be well suited for narrow bends (in homes or between automobiles), but it will increase the risk of striking a step in case of larger stairs and forces the carrier to exert great effort to hold the carrying rack high if he would like to avoid a fall or defect in the device. The uneven surface structures or overhanging tube connections increase the risk of getting caught in protruding structures, e.g., doorknobs. The uneven structures also make it difficult to clean the structure as a whole. The weight of the carrying rack itself increases the load for the carrier.

SUMMARY OF THE INVENTION

Consequently, there is a need in the state of the art for providing respirators that make possible a simple and ergonomic transportation from and to the patient as well as simple fastening of the oxygen cylinder when the respirator is coupled with an oxygen cylinder.

This object is accomplished by a respirator, which comprises a mounting device for a cylinder, preferably an oxygen cylinder, wherein the mounting device forms an upper housing half and a lower housing half of the respirator and comprises at least one grip, which makes transportation of the respirator possible, wherein the upper housing half and the lower housing half are provided with a connection mechanism, which connects the upper housing half and the lower housing half.

Stable mounting and safe transportation are achieved especially by advantageously arranging the cylinder between the two housing halves themselves. The cylinder is in contact with an upper jacket part and a lower jacket part of its cylinder body with the respective housing half. It is preferably arranged, furthermore, exactly between the two housing halves, which are preferably adapted to the cylinder jacket, and the two housing halves have no direct contact with one another in a preferred embodiment, but are connected to one another only via the connection mechanism or, in another embodiment, only by means of the cylinder.

According to the present invention, the respirator is of a compact design, so that the mounting device can receive the oxygen cylinder, i.e., it becomes the grip for the cylinder. Since the mounting device receives the cylinder, no separate carrying rack is necessary. The weight caused by additional frames is eliminated. Simple transportation to a patient is possible due to the compact design. The division of the mounting device into an upper housing half and a lower housing half supports the mounting of cylinders of different lengths and diameters. It is also possible to use cylinders without or with integrated cylinder head. The design makes it possible to replace the cylinder with a few movements of the hands reliably and rapidly. The cylinder can also be replaced such that this can be carried out without a tool, without opening the device, or without a special support.

The respirator may be able to be adapted to different cylinder diameters.

In one embodiment of the present invention, the grip is arranged on the upper housing half.

In another embodiment of the present invention a plurality of grips are provided in the respirator, which have different orientations in relation to one another in order to make different carrying positions possible.

Accordingly, vertical and horizontal carrying is made possible in the hand, so that it is possible to change over rapidly between different carrying positions depending on obstacles during use.

The mounting device may have a lightweight design, preferably made of a plastic material.

In another embodiment of the present invention, a belt system is provided for the respirator, and said belt system is connected to the mounting device and makes possible ergonomic transportation, so that no point loads occur during carrying.

The combination of the respirator and cylinder may be oriented now such that the grips are in the center of gravity in case of the combination with a cylinder of a predetermined volume, so that ergonomic, swinging-free carrying is made possible. Moreover, the belt system makes possible transportation on the shoulder or on the back and the hands of the ambulance paramedic/emergency physician are free. The center of gravity is located close to the body for carrying with reduced effort.

The fastening mechanism is designed such that when the cylinder is being replaced, the cylinder can be displaced vertically. Depending on the size of the cylinder, the center of gravity of the entire system can be shifted to below the middle position of the grip by means of this principle of operation. An optimally balanced carrying situation can thus be achieved.

The surface of the combination is designed such that no point loads occur during carrying, unlike in the above-mentioned prior-art systems, but the forces are applied to larger surfaces.

The connection mechanism connects the upper housing half and the lower housing half by means of magnetic force, preferably a permanent magnet with electric opposing magnet or with an electromagnet with power switch-off, by means of a tensioning means or by means of a frictional engagement between the mounting device and the cylinder, preferably pneumatically by suction cups or by a material pairing with soft elastic plastic of the mounting device.

A safety strap may be provided, which ensures protection of the cylinder head in the mounted position.

If no cylinder with integrated cylinder head is used, additional components are provided for the housing and/or cylinder, which ensure protection of the cylinder head in the mounted state, e.g., the special design of a grip as a safety strap.

A display means, an electronic interface or a sensor array may be arranged on the upper housing half. The sensor array may comprise a sensor system for the respiration of the patient to be respirated. For example, the tidal volume flow, respiration pressure, $CO_2$ concentration of the expired volume flow and other measured and manipulated variables of the patient, which are known per se, can thus be monitored and set.

In another embodiment of the present invention, the respirator is provided with a pair of mount means, wherein the pair of mount means comprises a holding element each, which is movable such that the pair of mount means meshes with corresponding guide elements.

The first holding element and the second holding element may be each designed in the form of a bolt, which is arranged at right angles to the longitudinal direction of the cylinder and is led at opposite ends along an elongated hole and is fixed in a first position by means of a prestressing element, preferably a spring, and moved into a second position.

The guide elements may be hook-shaped, which are arranged such that they are directed away from each other, and the guide elements can be overcome in the second position, so that the first holding element and second holding element come to lie in the guide elements in the first position.

In another embodiment of the present invention, the first holding element and the second holding element are arranged on the lower housing half and the guide elements are arranged on a base plate, which can be connected to a patient stretcher, a wall mount or a storage site in an ambulance.

In another embodiment of the present invention, the guide elements are arranged on the lower housing half and the first holding element and second holding element on a base plate, which can be connected to a patient stretcher, a wall mount or a storage site in an ambulance.

The respirator may be provided with a release mechanism in order to separate the first holding element and second holding element from the guide elements.

In another aspect, the present invention pertains to a mount for a respirator, which mount comprises a pair of mount means with a respective holding element each, which are movable such that the pair of mount means meshes with corresponding guide elements, which are arranged on a patient stretcher, a wall mount or a storage site in an ambulance.

The present invention will be explained in more detail below on the basis of exemplary embodiments with reference to the attached drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 12a is a side perspective view showing details of another mount for the respirator according to the present invention;

FIG. 12b is a side perspective view showing details of the mount for the respirator of FIG. 12a.

DESCRIPTION OF THE PREFERRED EMBODIMENTS

Figure 1:
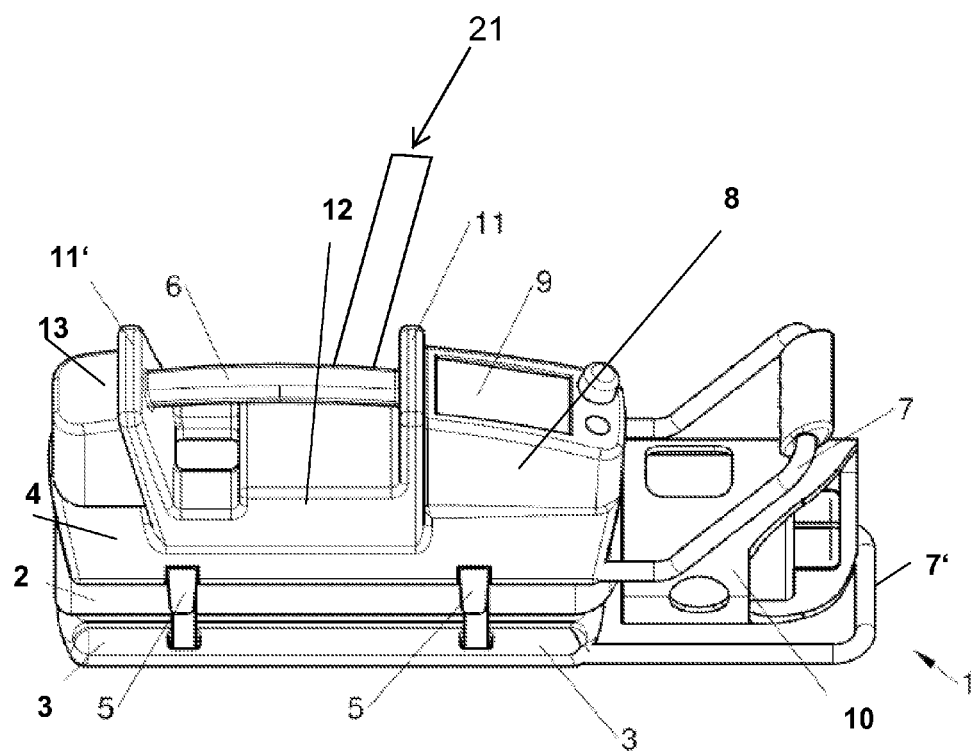
FIG. 1 is a side view of a respirator according to the present invention according to a first embodiment.

Referring to the drawings in particular, a first embodiment of the present invention is shown with reference to FIG. 1.

The respirator 1 has a mounting device for an oxygen cylinder 2, which forms a lower housing half 3 and an upper housing half 4 of the respirator 1. The two housing halves 3 and 4 are provided with a connection mechanism 5, which connects the upper housing half 4 and the lower housing half 3.

Upper housing half 4 and lower housing half 3 are preferably manufactured from a plastic material, so that the mounting device has a lightweight construction.

The embodiment shown in FIG. 1 embodies the connection mechanism 5 for connecting the upper housing half 4 to lower housing half 3 by means of a snap means, whose length can be adapted to different diameters of cylinder 2.

As is shown in FIG. 1, the respirator 1 has a first grip 6 and a second grip 7. The first grip 6 is arranged in the longitudinal direction of the cylinder 2 on the upper housing half 4 and permits vertical carrying of the respirator 1 with one hand. The first grip 6 is connected to two housing projections 11, 11' to the upper housing half 4, so that the member of the rescue team can reach with his hand under the grip 6 and grasp same. Respirator 1 and cylinder 2 may be oriented such that grip 6 is located in the center of gravity in case of a combination with a cylinder of a predetermined volume, so that ergonomic, swinging-free carrying is made possible. Cylinder 2 can be oriented for this when inserted within the upper housing half 4 and lower housing half 3 in the direction of the cylinder axis such that the center of gravity of the entire device is located in the area of grip 6. This can, of course, be achieved for cylinders 2 of different lengths and weight distributions.

The first grip 6 is joined on the upper side of the upper housing half 4 by a display means 9. The control and display means 9 makes, for example, information on the operation of the respirator 1 available, and this may also include the possibility of entering operating parameters. Furthermore, a wireless communication interface, which makes further processing of the data possible in a hospital, in the ambulance or in the rescue helicopter, may be arranged within the housing area 12. Housing area 12 may be designed for this as a cavity in order to accommodate the necessary electronic system. It is also possible to connect the display means 9 to the respirator 1 pivotably around a horizontal axis. As a result, the display means 9 can be brought into an optimal position for reading depending on the location of the operator in relation to the respirator 1. Another housing area 8, in which gas-carrying components, which are used to respirate the patient, may be arranged, is located under the display unit 9.

A battery 13, which supplies the above-mentioned electronic components with electricity, may also be arranged on the opposite side behind the housing projection 11'. Based on the fact that the housing is provided with the housing areas 8 and 12, the electric components may be accommodated in housing area 12 and the gas-carrying components in housing area 8, so that the housing construction ensures separation of oxygen-promoting combustion from electronic components as potential sources of ignition.

The second grip 7 is directed at right angles to the first grip 6, so that vertical carrying of the respirator 1 is made possible. In addition, the second grip 7 is arranged in the area of the cylinder head 10 and acts as a safety strap. The second grip 7 thus ensures protection of the cylinder head 10 in the mounted state. This is especially important when no cylinder with integrated cylinder head 10 is being used. However, it is also conceivable to bring about protection of the cylinder head 10 by additional components, preferably a safety strap 7', which are not used as grips at the same time.

Thus, respirator 1 has a plurality of grips, which are arranged in different orientations in relation to one another in order to make different carrying positions possible. Accordingly, vertical and horizontal carrying in the hand is made possible, so that it is possible to rapidly change over between different carrying positions during the use depending on the obstacles occurring.

In another embodiment of the present invention, a belt system 21, which is connected, for example, to the upper housing half 4, is provided in respirator 1. The belt system makes possible the ergonomic transportation of respirator 1, so that no point loads occur during carrying. In addition, the belt system makes transportation on the shoulder or on the back possible, so that the hands of the member of the rescue team/emergency physician are free. The center of gravity of respirator 1 is located close to the body for carrying with reduced effort.

Figure 2:
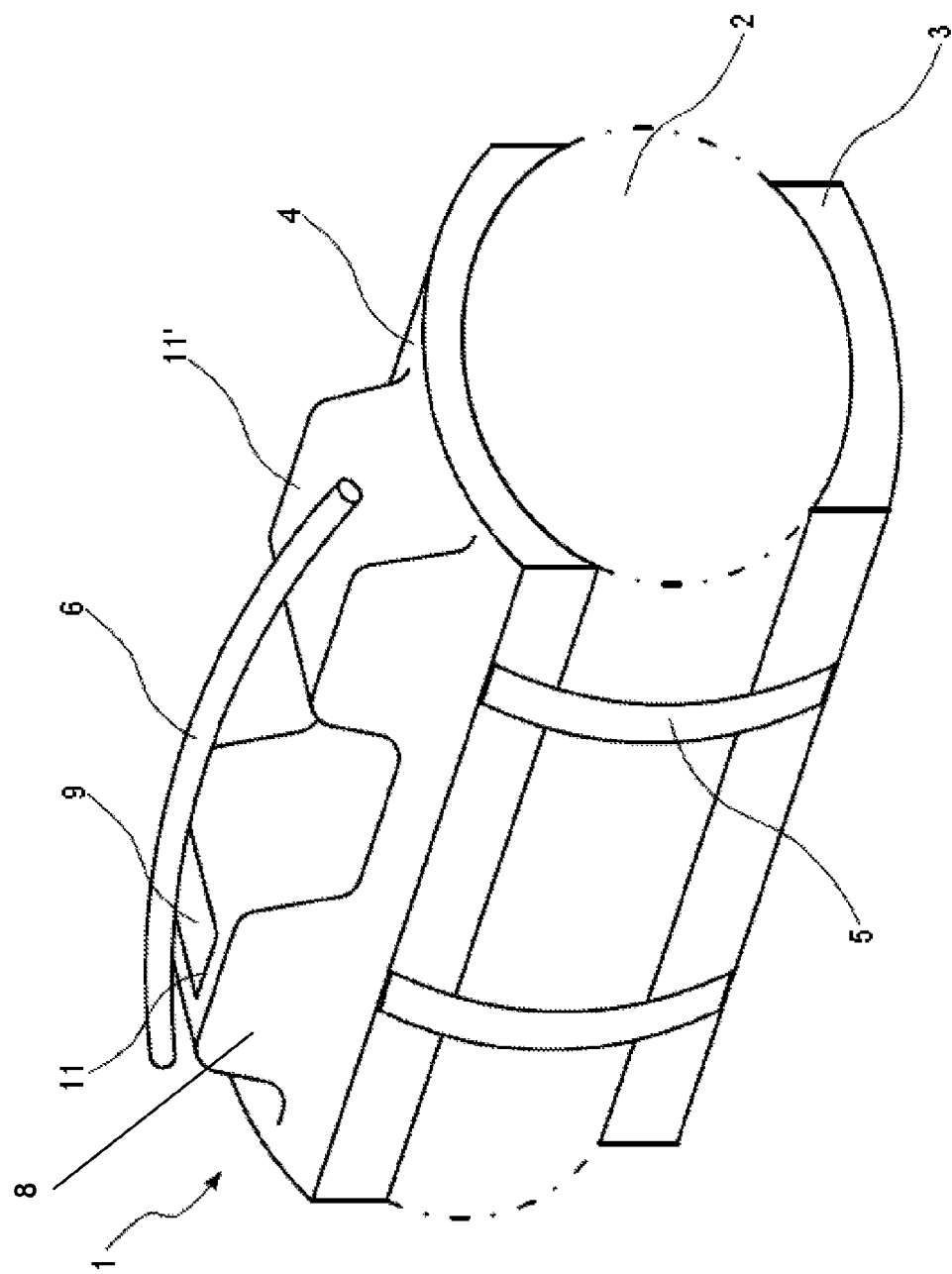
FIG. 2 is a side view of a respirator according to the present invention according to a second embodiment.

A second embodiment of the present invention will be explained below with reference to FIG. 2.

Respirator 1 has again a mounting device for an oxygen cylinder 2, which forms the lower housing half 3 and upper housing half 4 of respirator 1. The two housing halves 3 and 4 are provided with the connection mechanism 5, which connects the upper housing half 4 and the lower housing half 3 by means of a tensioning belt.

The first grip 6 is arranged in the longitudinal direction of cylinder 2 on the upper housing half 4 and permits horizontal carrying of respirator 1 in the hand of a member of the rescue team. The first grip 6 is connected to a first housing projection 11 and a second housing projection 11' on the upper housing half 4, so that the hand of the member of the rescue team can reach under and grasp grip 6.

The control and display means 9 is arranged on housing area 8 on the upper side. As was explained before, the display means 9 makes available information on the operation of respirator 1 and permits operating parameters to be entered. Display means 9 can exchange data within the system as well as with external devices by means of cables or by means of wireless communication interfaces. Furthermore, further electronic components may also be arranged within the first housing projection 11 and/or second housing projection 11'.

The design of respirator 1 according to FIG. 2 will be illustrated once again below with reference to FIG. 3.

Figure 3:
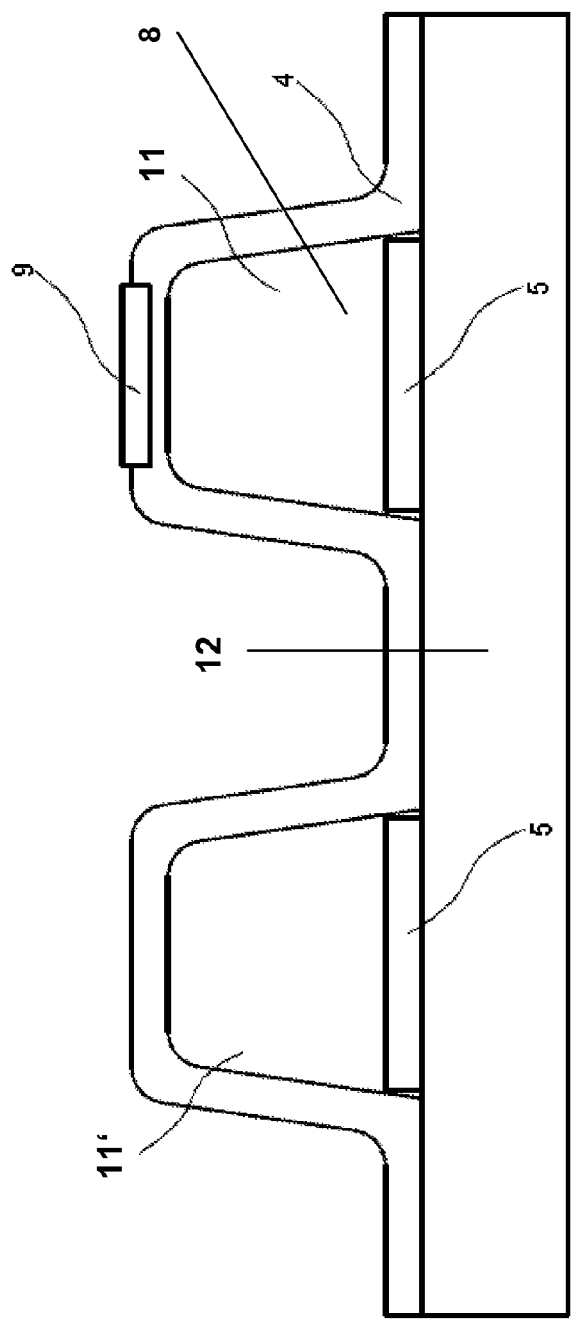
FIG. 3 is a sectional view of the respirator according to the present invention according to FIG. 2.

FIG. 3 shows a section through the upper housing half 4. The control and display means 9 on housing area 8 makes possible the simple reading of the information being displayed or the entry of operating parameters. Due to the housing areas 8 and 12 being designed as cavities, a simple possibility is offered for providing two areas separated in space in the housing, which establish the above-mentioned gas-tight separation between gas-carrying components and the electronic system. The part of the housing upper part that lies directly on cylinder 2 can close the housing areas 8 and 12 upwardly and receive and guide the connection mechanism 5 in the form of tensioning belts in the downward direction.

A variant of the present invention will be explained below with reference to FIG. 4.

Figure 4:
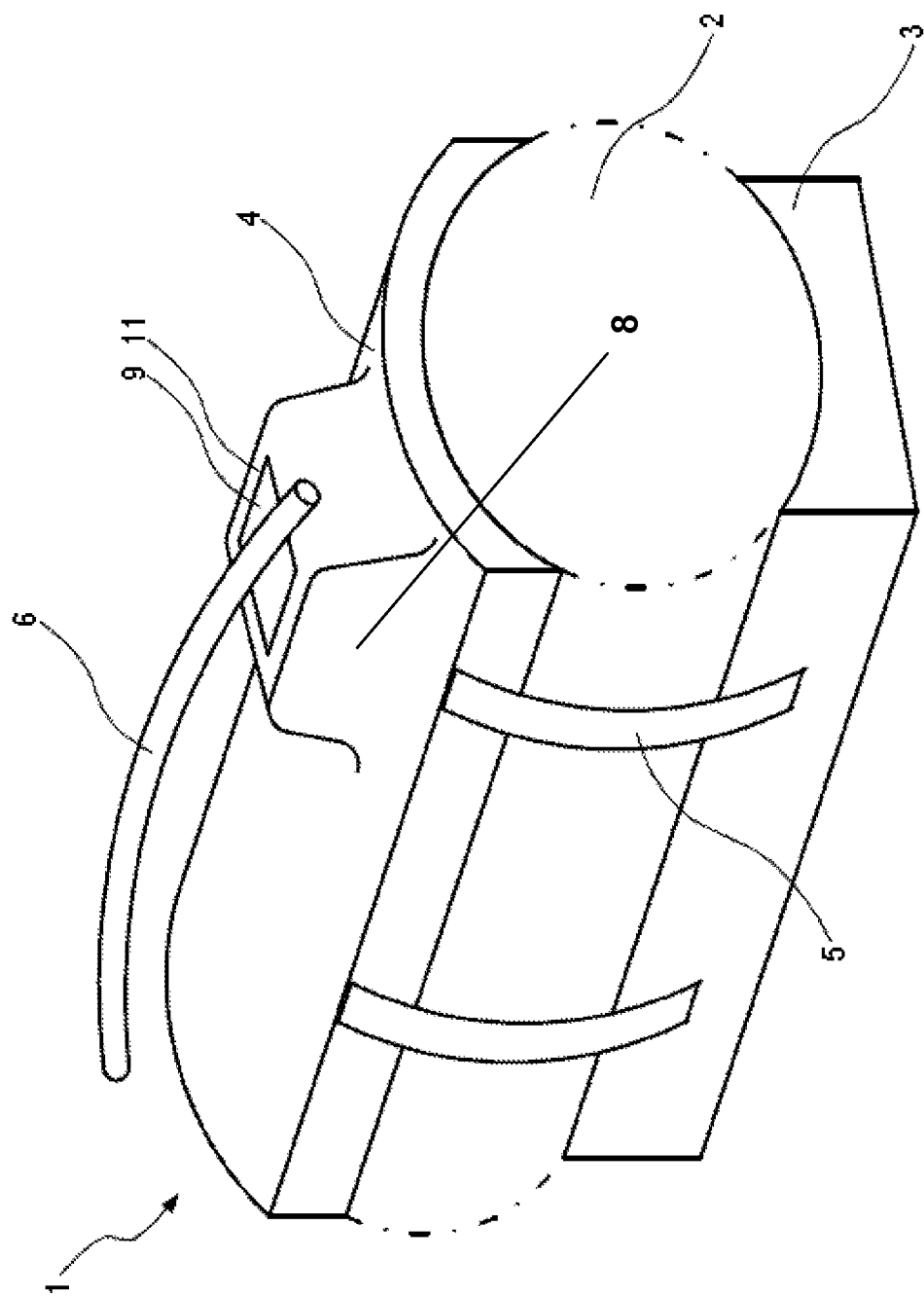
FIG. 4 is a side view of the respirator according to the present invention according to a third embodiment.
Figure 5:
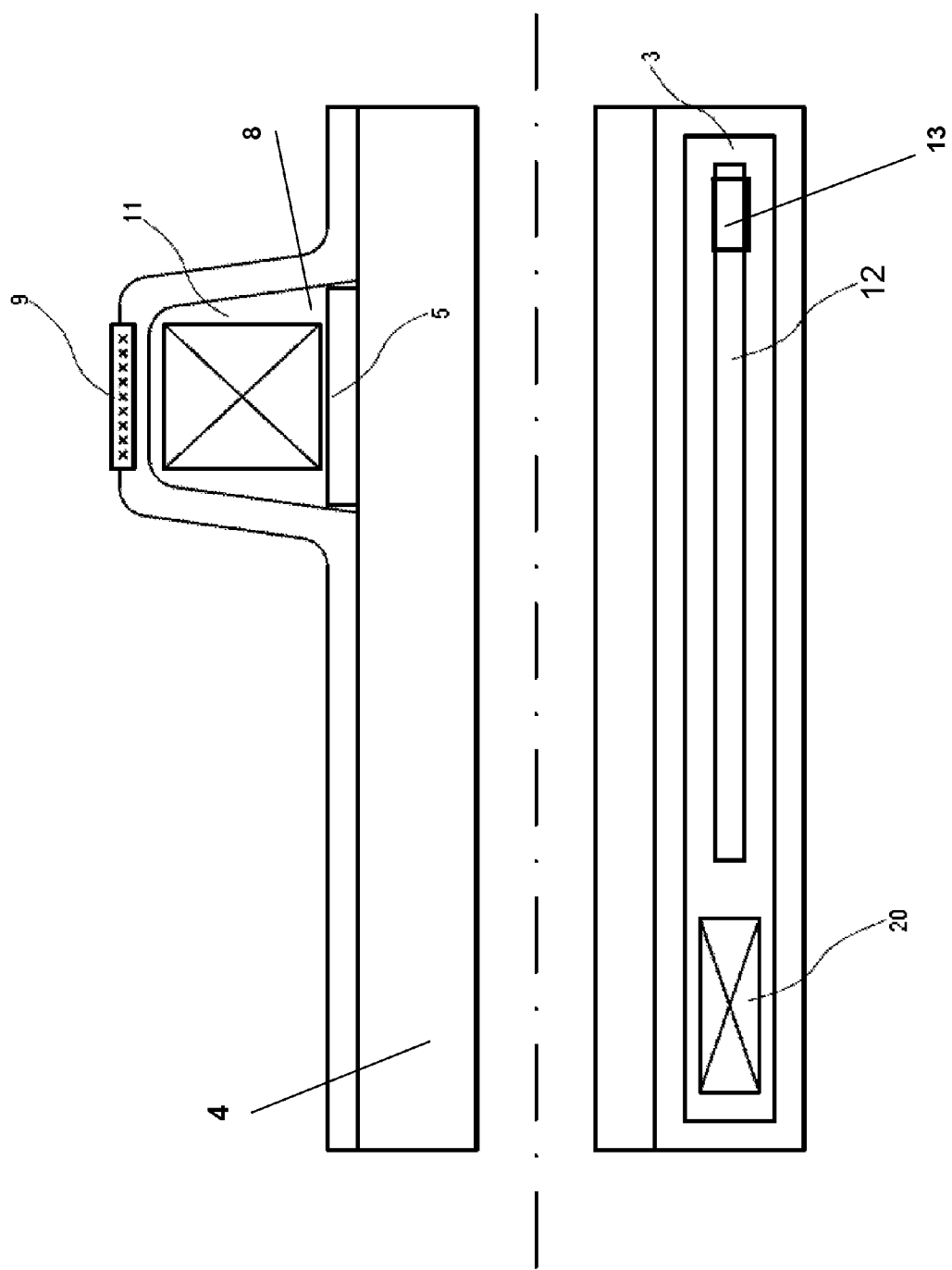
FIG. 5 is a sectional view of the respirator according to the present invention according to FIG. 4.

FIG. 5 shows a section through the upper housing half 4 and the lower housing half 3 of the variant according to FIG. 4. The control and display means 9 on housing area 8 makes possible the simple reading of the information being displayed and the entry of operating parameters. The current-carrying components and battery 13 are accommodated in the lower housing half 3 in this embodiment variant. The separation between the electronic system and gas-carrying components is fully accomplished here.

Figure 6:
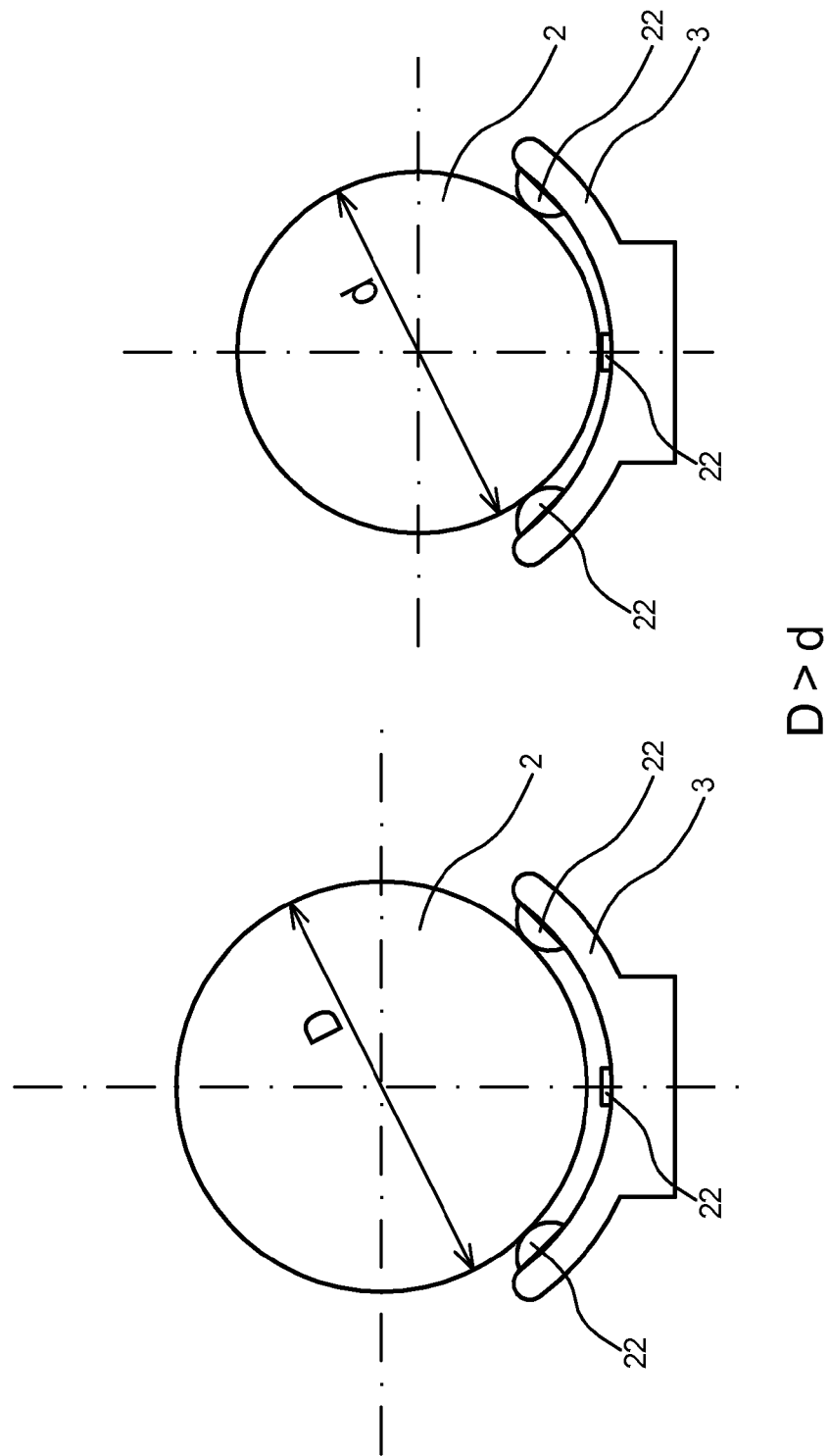
FIG. 6 is a sectional view of a detail of a cylinder mount for the respirator according to the present invention.

FIG. 6 shows the adaptation of the mounting device to cylinders with different diameters. The view on the left shows a sectional view of a cylinder 2 with a diameter D in a sectional view, which is arranged on the lower housing half 3. The view on the right shows a sectional view of another cylinder 2 with a diameter d, which is smaller than diameter D, which is arranged on the lower housing half 3. To make it possible to insert cylinders 2 with different diameters, elevated structural elements 22 are arranged on the lower housing half 3.

As is shown in FIG. 6, a total of three elevated structural elements 22 are provided, but a different number of elevated structural elements 22, for example, two or four, are also possible. The elevated structural elements 22 are oriented in the longitudinal direction on the lower housing half 3 and may be designed, for example, as integral components of the lower housing half 3. However, it is also conceivable to connect the elevated structural elements 22 to the lower housing half 3. Other possibilities of adapting the mounting device to cylinders with different diameters could be embodied, for example, by inflatable components or by parts that are to be inserted, e.g., plastic foam components. Furthermore, the above-described embodiment variants may also be applied to the upper housing half 4.

Cylinder 2 must be fixed in the mounting device. Different possibilities are available for this, which will be explained below with reference to FIGS. 7a through 7c.

Figure 7C:
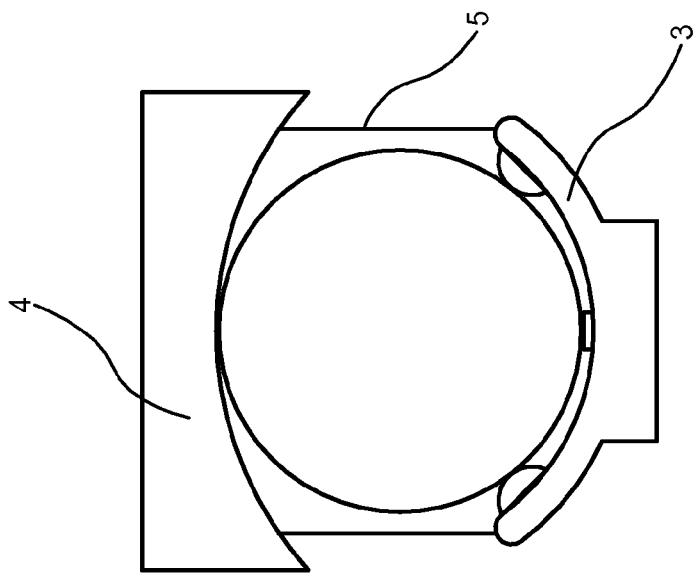
FIG. 7c is a schematic sectional view of details of a cylinder mount for the respirator according to the present invention.
Figure 7B:
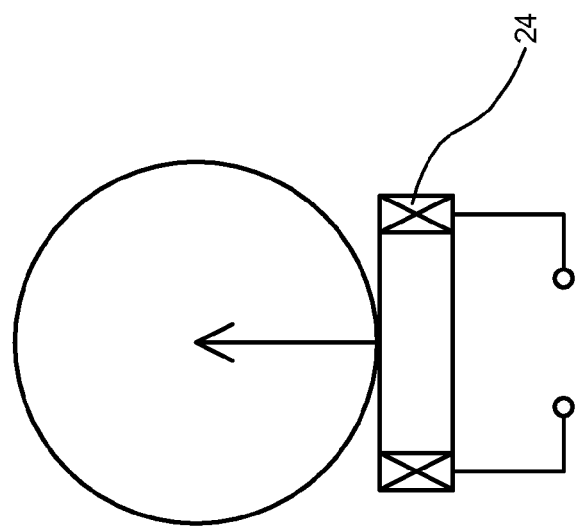
FIG. 7b is a schematic sectional view of details of a cylinder mount for the respirator according to the present invention.
Figure 7A:
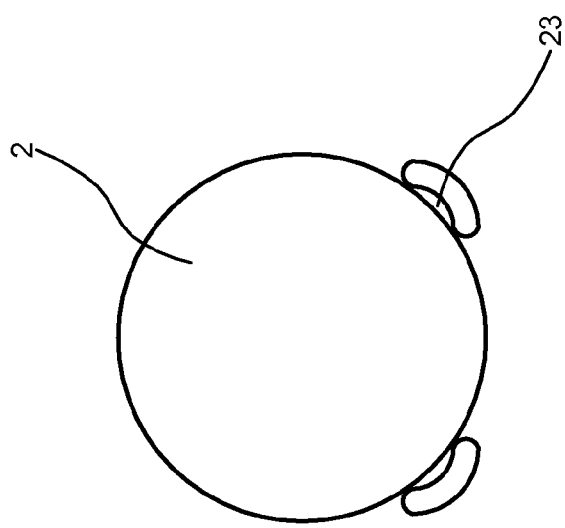
FIG. 7a is a schematic sectional view of details of a cylinder mount for the respirator according to the present invention.

According to FIG. 7a, frictional engagement is established between the housing and the cylinder pneumatically by suction cups 23. The suction cups 23 are arranged, for example, on the lower housing half 3.

FIG. 7b shows that the cylinder 2 is fixed by magnetic force. A permanent magnet with opposing electric magnet could be used for this to abolish the normal force when changing the cylinder. Provisions are also made for using an electromagnet 24 with power switch-off to abolish the force.

According to FIG. 7c, a frictional engagement is established between the housing and cylinder by material pairing with soft elastic plastic for the lower housing half 3 and/or upper housing half 4 as well as tightening of a contacting strap, which is part of the connection mechanism 5. The soft elastic plastic ensures that the lower housing half 3 and/or upper housing half 4 surrounds the cylinder after tightening the connection mechanism 5, so that this is fixed in the mounting device.

Figure 8:
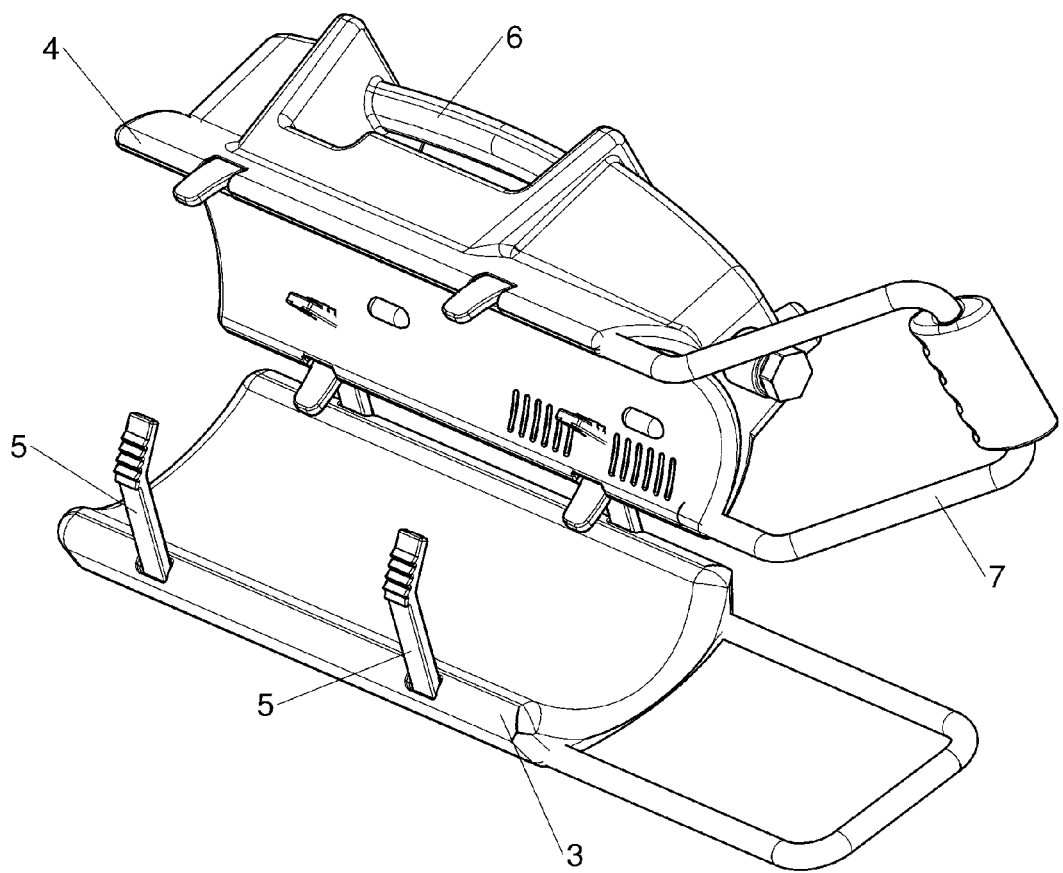
FIG. 8 is a side view of a respirator according to the present invention in the opened state.

The division of the mounting device into upper housing half 4 and lower housing half 3 supports the accommodation of cylinders of different lengths and diameters. The makes it possible to carry out the replacement of a cylinder reliably and rapidly with few movements of the hands. The replacement of the cylinder can be carried out such that this is possible without a tool, without opening the device, without removal from a wall mount or mount or a special support. This can be seen, for example, from FIG. 8, which shows an opened mounting device. After inserting a cylinder, the upper housing half 4 is placed over the lower housing half 3 and they are connected to one another by means of the connection mechanism 5.

Provisions are often made during the use of the respirator 1 for the respirator 1 to be connected to a patient stretcher, a wall mount or a storage site in an ambulance, which requires a mount.

Figure 9:
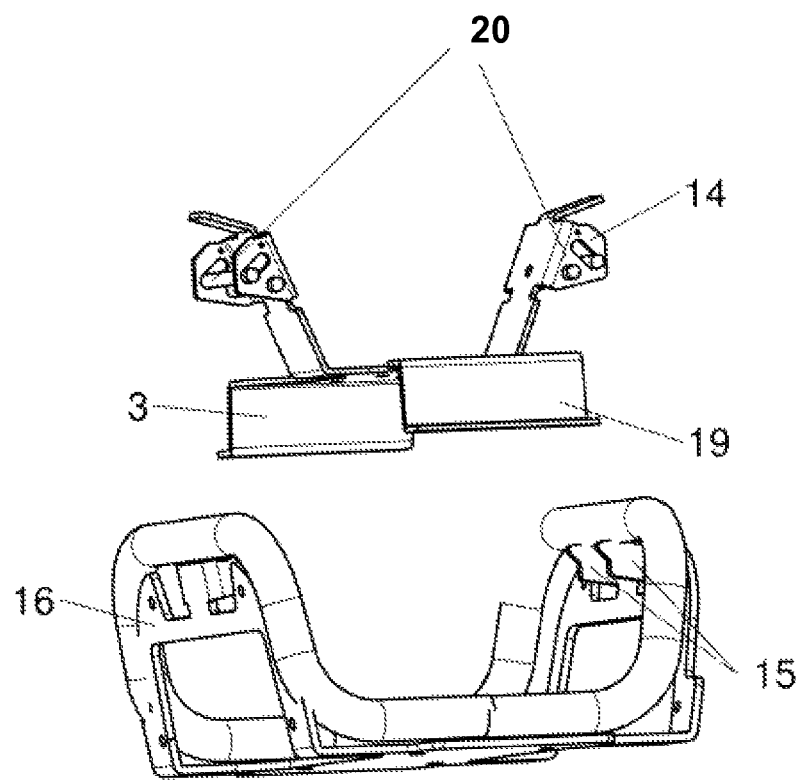
FIG. 9 is a side view of a detail of a mount for the respirator according to the present invention.

One possibility for a mount is shown in FIG. 9. FIG. 9 shows a view of the lower housing half 3 of the respirator 1 with a basic body 16, which is connected to a patient stretcher, a wall mount or a storage site in an ambulance or rescue helicopter. Respirator 1 is connected to the basic body 16 by means of the mount.

To hold the respirator 1 with a basic body 16, the lower housing half 3 is provided with a pair of mount means. The pair of mount means comprises a holding element 20 each, which is designed in the form of a bolt, which is arranged in the longitudinal direction of the cylinder.

The holding elements 20 are guided at opposite ends along an elongated hole and fixed by means of a prestressing element, preferably a spring, in a first position and can be moved into a second position. The pair of holding means on the lower housing half 3 meshes with corresponding guide elements 15 on the housing body 16.

The meshing of the holding elements 20 with the guide elements 15 on the basic body 16 will be explained in more detail with reference to FIGS. 10*a* through 10*d*.

The holding elements 20 are mounted axially in the respirator 1 and can move along the elongated hole 14 in the device wall 19. If the respirator 1 is not in the basic body 16 of the wall mount, the holding elements 20 designed as bolts are in a first position (stop position) at the end of the elongated hole 14, as is shown in FIG. 10*a*, due to the spring force of spring 18.

Figure 10:
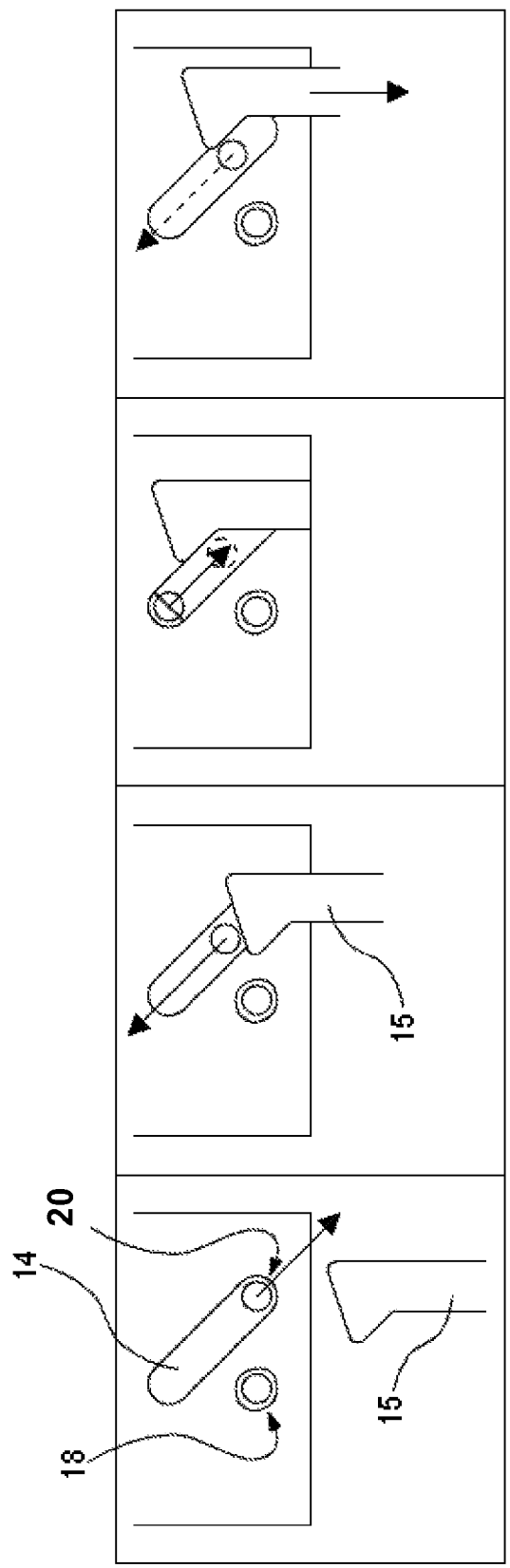
FIG. 10a is a schematic side view of details of another mount for the respirator according to the present invention.
FIG. 10b is a schematic side view of details of another mount for the respirator according to the present invention.
FIG. 10c is a schematic side view of details of another mount for the respirator according to the present invention.
FIG. 10d is a schematic side view of details of another mount for the respirator according to the present invention.

If the respirator 1 is now inserted into the basic body 16 of the wall mount, as is shown in FIG. 10*b*, a force is applied to the holding elements 20 designed as bolts by the geometric contour of the guide elements 15 at the wall mount. As a result, the holding elements 15 move along the elongated hole 14 and against the spring force.

When considering the two holding elements 20 designed as bolts, it is seen that these are pushed apart. The holding elements 20 slide over the outer edge of the hook-shaped guide elements 15 and are then pushed again in the other direction along the elongated hole 14 based on the spring force, as this is shown in FIG. 10*c*. The two holding elements 20 are moving towards one another. The guide elements 15 can consequently be overcome in a second position of the holding elements 20, so that the holding elements 20 come to lie in the guide elements 15 in the first position.

When attempting now to pull the respirator 1 out of the mount, as this is shown in FIG. 10*d*, the pulling force of the guide elements acts on the two holding elements 20, which can in turn move only along the elongated holes 14, so that force is transmitted to the wall mount. If a force is applied in the z direction (at right angles to the drawing plane), the force is transmitted by the guide elements 15 and the lateral device walls 19.

The symmetrical design of the mount and locking mechanism offers the advantage that the respirator 1 can be inserted in different orientations into the basic body 16 of the wall mount. In addition, the mechanism offers the advantage that the respirator 1 can be inserted into the wall mount both from the top and laterally. It thus becomes possible for the user to arrange the respirator 1 flexibly and ergonomically in different orientations in the rescue transport vehicle or on any other wall.

Figure 11:
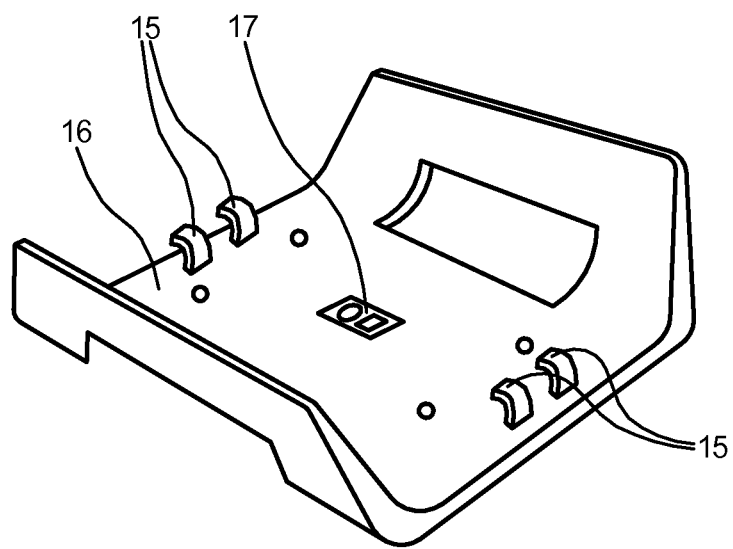
FIG. 11 is a side view of a detail of another mount for the respirator according to the present invention.

As is shown in FIG. 11, the basic body 16 of the wall mount is equipped in this exemplary embodiment with electric contacts as terminals 17 on the side or support surface of the respirator 1, via which the internal battery of the device is charged and a possible data transfer takes place. Charging by means of induction coil is conceivable as well. Other pneumatic plug-type connections or ports may also be provided in the wall mount for the oxygen supply of the device (not shown in FIG. 11). This connection may be embodied, e.g., by means of existing plug-type connections.

In another exemplary embodiment, the guide elements 15 of the mount are embodied on the lateral flanks, as is shown in FIG. 12*a* and FIG. 12*b*, rather than on the bottom plate of the mount. The holding elements are analogously also arranged on the sides of respirator 1.

In another exemplary embodiment, the spring-loaded, guided holding elements 20 and the guide elements 15 are transposed with one another, i.e., the holding elements 20 designed as bolts are located in the wall mount and the guide elements at respirator 1.

To remove the respirator 1 from the wall mount with one hand, the respirator 1 is equipped with a release mechanism in grip 6. This mechanism pulls the two holding elements 20 designed as bolts upwards in the direction of the elongated hole, see FIG. 10*d*, arrow drawn in broken line. The guide elements of the wall mount are thus released and the respirator 1 can be removed. This mechanism can be actuated by means of a mechanical connection (e.g., Bowden cable) or, e.g., also by means of a pneumatic, magnetic, hydraulic or electric connection. The electric and pneumatic contacts are broken during the removal of the respirator 1 from the wall mount.

In case of the exemplary embodiment with mutually transposed holding elements 20 designed as bolts and guide elements, the release mechanism is located in the wall mount instead of in the respirator 1. The user actuates in this embodiment at first the release mechanism on the wall mount, after which the respirator 1 is grasped and lifted out of the wall mount. To guarantee removal with one hand and reliable positioning of the respirator 1 in this exemplary embodiment as well after opening the holding mechanism, the respirator 1 is held passively in the wall mount in the horizontal and vertical position. A holding mechanism (e.g., a mechanical mechanism using a hook, a magnetic or electric mechanism), which holds the respirator 1 with the locking mechanism opened, is used for this.

To prevent the locking mechanism from being opened by the user unnoticeably, the release mechanism must either close again after opening with a time delay of a few seconds or display the actual state by an indicator connected to the release mechanism. The indicator may be designed, e.g., as a mechanical indicator (signal transmitter moved by the release mechanism and highlighted in color) or as an electric indicator (warning light controlled by the release mechanism).

The principle of the wall mount described in the exemplary embodiments shown above can also be applied to the flexibly mountable mount at a stretcher. The principle of the mount and locking mechanism is taken over for this. In addition, the mount is collapsible, so that it is in contact with the stretcher during non-use in a compact manner. The connection between the stretcher and the mount can be achieved, e.g., by means of a screw connection.

Figure 13:
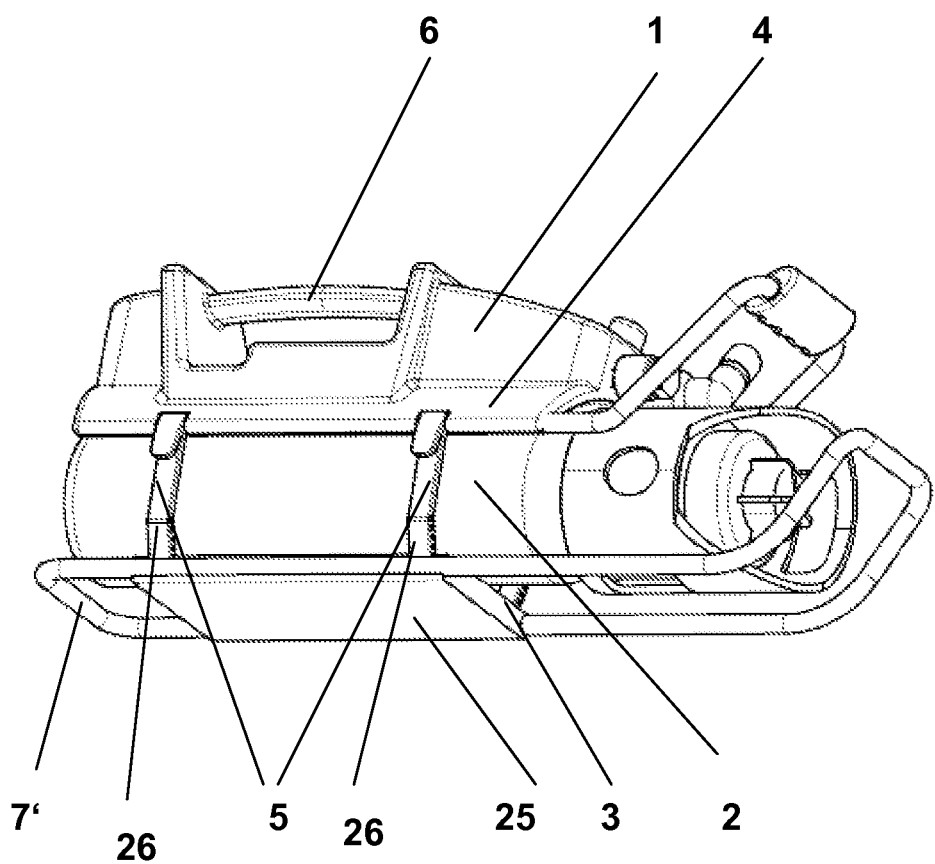
FIG. 13 is a perspective view of another embodiment of the respirator according to the present invention.

FIG. 13 shows another embodiment of the respirator according to the present invention. Cylinder 2 is located between lower housing half 3 and upper housing half 4, with the respirator 1 being integrated in the upper housing half 4. Grip 6 is located on the upper side of upper housing half 4. Lower housing half 3 comprises a circumferential safety strap 7', which is reinforced by a bottom plate 25 in the area of cylinder 2. The cylinder 2 is held between housing halves 3 and 4 by means of two fastening belts 26 and connection mechanisms 5 holding the fastening belts 26 together. An especially simple design of the lower housing half 3 is obtained due to the circumferential safety strap 7' in conjunction with the bottom plate 25. Cylinders 2 with different diameters can be connected to the respirator 1 in an especially simple manner by the fastening belts 26, whose length can be adapted in a simple manner.

While specific embodiments of the invention have been shown and described in detail to illustrate the application of the principles of the invention, it will be understood that the invention may be embodied otherwise without departing from such principles.

LIST OF REFERENCE NUMBERS

1 Respirator
2 Cylinder
3 Lower housing half

4 Upper housing half
5 Connection mechanism
6 Grip
7 Other grip 7', safety strap
8 Housing area for gas-carrying components
9 Display device
10 Cylinder head
11 Housing projection
11' Housing projection
12 Housing area for current-carrying components
13 Battery
14 Elongated hole
15 Guide element
16 Basic body
17 Port
18 Spring
19 Device wall
20 Holding element
21 Electronic components
22 Elevated element
23 Suction cup
24 Magnet
25 Bottom plate
26 Tightening belt

What is claimed is:

1. A respirator comprising a mounting device for a breathing gas cylinder, the mounting device comprising:
an upper housing half;
a lower housing half, said lower housing half being a separate distinct movable part from said upper housing half, said lower housing half comprising elevated structural elements, each of said elevated structural elements being located at a spaced location from another one of said elevated structural elements;
a grip for grasping the mounting device to transport the respirator; and
a connection mechanism provided with the upper housing half and the lower housing half and connecting the upper housing half and the lower housing half at least indirectly to one another, wherein the cylinder is located in a mounted position between the upper housing half and the lower housing half, said elevated structural elements being in contact with the cylinder with the cylinder in the mounted position, said lower housing half comprising a lower half housing portion connected to said elevated structural elements, said lower housing half portion comprising a shape corresponding to a shape of the cylinder, said connection mechanism fixing a position of said upper housing half relative to said lower housing half and fixing the cylinder therebetween with the cylinder in the mounted position, said connection mechanism comprising a strap, at least a portion of said strap bridging an opening between said upper housing half and said lower housing half with the cylinder in the mounted position, the mounting device being adaptable to different cylinder diameters by providing the elevated structural elements to achieve adaptability to the different cylinder diameters, wherein a length of said portion of said strap varies based on different cylinder diameters, said lower housing half being freely movable independently from said upper housing half, said elevated structural elements comprising a first structural element, a second structural element and a third structural element, said second structural element being arranged between said first structural element and said third structural element, said first structural element and said third structural element defining a first arrangement of structural elements for engaging the cylinder when the cylinder is mounted between said lower housing half and said upper housing half, the cylinder having a first cylinder diameter, said first structural element, said second structural element and said third structural element defining a second arrangement of structural elements for engaging another cylinder when the another cylinder is mounted between said lower housing half and said upper housing half, the another cylinder comprising a second cylinder diameter, said second cylinder diameter being less than said first cylinder diameter, wherein at a given instance only one cylinder is arranged between said lower housing half and said upper housing half.

2. A respirator in accordance with claim 1, wherein the grip is arranged on the upper housing half, wherein said lower housing half and said upper housing half surround the cylinder after tightening the strap such that the cylinder is fixed between said lower housing half and said upper housing half.

3. A respirator in accordance with claim 1, further comprising another grip to provide a plurality of grips which have different orientations in relation to one another in order to make different carrying positions possible, at least one of said lower housing half and said upper housing half comprising a storage compartment for carrying electronics, wherein one or more of said lower housing half and said upper housing half has another storage compartment for storing gas carrying components.

4. A respirator in accordance with claim 1, wherein the mounting device comprises a plastic material, said upper housing half and said lower housing half defining an opening with the cylinder located in the mounted position, said at least said portion of said strap extending between said upper housing half and said lower housing half, said at least said portion of said strap being located adjacent to the cylinder.

5. A respirator in accordance with claim 1, further comprising a belt system connected to the mounting device, the belt system including an ergonomic transportation interface distributing load so that no point loads occur during carrying.

6. A respirator in accordance with claim 1, wherein the connection mechanism comprises at least one of:
a magnetic connection means connecting the upper housing half and the lower housing half by magnetic force and comprising at least one of a permanent magnet with opposing electric magnet or an electromagnet with power switch-off;
a tensioning means applying tension for connecting the upper housing half and the lower housing half; and
a frictional engagement between the mounting device and the cylinder comprising one of suction cups and material pairing with soft elastic plastic of the mounting device frictionally engaging the cylinder.

7. A respirator in accordance with claim 1, further comprising a safety strap ensuring protection of a cylinder head in the mounted state.

8. A respirator in accordance with claim 1, further comprising a pair of holding means with a first holding element and a second holding element and corresponding guide elements, said first holding element and said second holding element being connected to said lower housing half, said first holding element being located opposite said second holding element, each holding element being movable to mesh with the corresponding guide element, wherein said first structural element and said third structural element engage the cylinder with the first cylinder diameter when the cylinder is mounted between the first housing half and the second housing half, said second structural element being located at a spaced location from the cylinder with the first cylinder diameter when the cylinder is mounted between the first housing half and the second housing half, said first structural element, said second structural element and said third structural element engaging said another cylinder when the another cylinder is mounted between the first housing half and the second housing half.

9. A respirator in accordance with claim 8, wherein the first holding element and the second holding element each form a bolt, arranged in a longitudinal direction of the cylinder and guided at opposite ends along an elongated hole and fixed in a first position by means of a prestressing element and moved into a second position against the force of the prestressing element, said first holding element being arranged on one side of said lower housing half, said second holding element being arranged on another side of said lower housing half, said lower housing half comprising another lower housing half portion, said another lower housing half portion comprising a lower planar surface.

10. A respirator in accordance with claim 9, wherein the guide elements are of a hook-shaped design and are arranged such that they are directed away from each other, wherein said guide elements can be overcome in the second position, so that the first holding element and second holding element come to lie in the guide elements in the first position.

11. A respirator in accordance with claim 8, further comprising a basic body connectable to a patient stretcher, a wall mount site or a storage site in an ambulance or in a rescue helicopter, wherein the first holding element and the second holding element are arranged on the lower housing half and the guide elements are arranged on the basic body.

12. A respirator in accordance with claim 8, further comprising a basic body connectable to a patient stretcher, a wall mount site or a storage site in an ambulance or in a rescue helicopter, wherein the guide elements are arranged on the lower housing half and the first holding element and the second holding element are arranged on the basic body.

13. A respirator in accordance with claim 8, further comprising a release mechanism in order to separate the first holding element and the second holding element from the guide elements.

14. A respirator mount comprising:
a pair of mount means, each of said pair of mount means comprising a holding element, the holding elements each with corresponding guide elements which can be moved when said holding elements engage said corresponding guide elements such that the holding elements mesh with the corresponding guide elements, the holding elements and guide elements being connected to a mounting device for a breathing gas cylinder of a patient stretcher, a wall mount site, or a storage site in an ambulance, or in a rescue helicopter, or a respirator, the mounting device comprising:
an upper housing half;
a lower housing half freely movable independent of movement of said upper housing half, said lower housing half comprising a lower housing half arcuate shape;
structural elements connected to said lower housing half, each of said structural elements extending in a longitudinal direction of said lower housing half, each of said structural elements being located at a spaced location from one another, said structural elements comprising a first structural element, a second structural element and a third structural element, said second structural element being arranged between said first structural element and said third structural element, wherein each of said first structural element and said third structural element has a height that is greater than a height of said second structural element;
a grip connected to one of said upper housing half and said lower housing half for grasping the mounting device to transport the respirator; and
a connection mechanism provided with the upper housing half and the lower housing half connecting the upper housing half and the lower housing half at least indirectly to one another, wherein the cylinder is located in a mounted position between the upper housing half and the lower housing half, said lower housing half arcuate shape corresponding to a shape of a portion of the cylinder, said structural elements engaging the cylinder, said connection mechanism comprising a strap, said strap fixing the upper housing half relative to the lower housing half with the cylinder located in the mounted position, said lower housing half being located at a spaced location from said upper housing to define a housing opening, at least a portion of said strap bridging said opening with the cylinder located in the mounted position.

15. A respirator mount in accordance with claim 14, further comprising a basic body connectable to the patient stretcher, the wall mount site or the storage site in the ambulance or in the rescue helicopter wherein a first holding element and a second holding element are arranged on the lower housing half and the guide elements are arranged on the basic body, wherein said strap is in direct contact with said lower housing half and said upper housing half with the cylinder located in the mounted position, at least one of said lower housing half and said upper housing half comprising a storage compartment for carrying electronics, wherein one or more of said lower housing half and said upper housing half has another storage compartment for storing gas carrying components said first structural element and said third structural element defining a first arrangement of structural elements for contacting the cylinder when the cylinder is mounted between the first housing half and the second housing half, the cylinder having a first cylinder diameter, said first structural element, said second structural element and said third structural element defining a second arrangement of structural elements for contacting another cylinder when the another cylinder is mounted between the first housing half and the second housing half, the another cylinder having a second cylinder diameter, said second cylinder diameter being less than said first cylinder diameter, wherein said first structural element and said third structural element engage the cylinder with the first cylinder diameter when the cylinder is mounted between the first housing half and the second housing half, said second structural element being located at a spaced location from the cylinder with the first cylinder diameter when the cylinder is mounted between the first housing half and the second housing half, said first structural element, said second structural element and said third structural element engaging said another cylinder when the another cylinder is mounted between the first housing half and the second housing half, said lower housing half comprising a lower housing half portion, said lower housing half portion comprising a lower planar surface, said pair of mount means being connected to said lower housing half, wherein at a given instance only one cylinder is arranged between said lower housing half and said upper housing half.

16. A respirator mount in accordance with claim 14, further comprising a basic body connectable to the patient stretcher, the wall mount or the storage site in the ambulance or in the rescue helicopter, wherein the guide elements are arranged on the lower housing half and a first holding element and a second holding element are arranged on the basic body, wherein said at least said portion of said strap is located adjacent to the cylinder.

17. A respirator system comprising:
a respirator comprising:
a breathing gas cylinder, said breathing gas cylinder comprising a breathing gas cylinder contour; and
a breathing gas cylinder mounting device comprising:
an upper housing half;
structural elements, each of said structural elements being located at a spaced location from one another, said structural elements comprising a first structural element, a second structural element and a third structural element, said second structural element being arranged between said first structural element and said third structural element, said first structural element comprising a first structural element outer cylinder contact surface, said second structural element comprising a second structural element outer cylinder contact surface, said third structural element comprising a third structural element outer cylinder contact surface;
a lower housing half, said structural elements being connected to said lower housing half, said lower housing half comprising a lower housing half portion facing in a direction of the upper housing half, said lower housing half portion comprising a lower housing half portion contour, said lower housing half portion contour being the same as said breathing gas cylinder contour, said first structural element outer cylinder contact surface being located at a first distance from said lower housing half portion, said second structural element outer cylinder contact surface being located at a second distance from said lower housing half portion, said third structural element outer cylinder contact surface being located at a third distance from said lower housing half portion, said first distance and said third distance being greater than said second distance;
a grip fixed to one of said upper housing half and said lower housing half for grasping the mounting device to transport the respirator; and
a connection mechanism provided with the upper housing half and the lower housing half and connecting the upper housing half and the lower housing half at least indirectly to one another, wherein the cylinder is located in a mounted position between the upper housing half and the lower housing half, said connection mechanism comprising a strap, said strap fixing said upper housing half relative to said lower housing half with the cylinder in the mounted position and said strap fixing the cylinder to said upper housing half and said lower housing half with the cylinder in the mounted position, said structural elements engaging the cylinder with the cylinder in the mounted position, said upper housing half and said lower housing half defining an opening with the cylinder in the mounted position, at least a portion of said strap bridging said opening with the cylinder in the mounted position; and
a pair of mount means, each of said pair of mount means comprising a holding element, the holding elements each with corresponding guide elements which can be moved when said holding elements contact said corresponding guide elements such that the holding elements mesh with the corresponding guide elements, the pair of mount means being connected to the mounting device and a patient stretcher, a wall mount site or a storage site in an ambulance, or rescue helicopter.

18. A respirator system in accordance with claim 17, further comprising a basic body connectable to the patient stretcher, the wall mount site or the storage site in the ambulance or in the rescue helicopter wherein a first holding element and a second holding element are arranged on the lower housing half and the guide elements are arranged on the basic body, wherein said at least said portion of said strap is located directly adjacent to the cylinder with the cylinder in the mounted position, said first structural element and said third structural element defining a first arrangement of structural elements for supporting the cylinder when the cylinder is in the mounted position, the cylinder comprising a first cylinder diameter, said first structural element, said second structural element and said third structural element defining a second arrangement of structural elements for supporting another cylinder when the another cylinder is mounted between said lower housing half and said upper housing half, said another cylinder comprising a second cylinder diameter, said second cylinder diameter being less than said first cylinder diameter, wherein said first structural element and said third structural element engage the cylinder with the first cylinder diameter when the cylinder is in the mounted position, said second structural element being located at a spaced location from the cylinder with the first cylinder diameter, said first structural element, said second structural element and said third structural element engaging said another cylinder when the another cylinder is mounted between said first housing half and said second housing half, said lower housing half comprising another lower housing half portion, said another lower housing half portion comprising a lower planar surface, said pair of mount means being connected to said lower housing half, wherein at a given instance only one cylinder is arranged between said lower housing half and said upper housing half.

19. A respirator system in accordance with claim 17, further comprising a basic body connectable to the patient stretcher, the wall mount site or the storage site in the ambulance or in the rescue helicopter, wherein the guide elements are arranged on the lower housing half and a first holding element and a second holding element are arranged on the basic body, at least one of said lower housing half and said upper housing half comprising a storage compartment for carrying electronics, wherein one or more of said lower housing half and said upper housing half has another storage compartment for storing gas carrying components, said first structural element and said third structural element defining a first cylinder support configuration for supporting the cylinder when the cylinder is in the mounted position, the cylinder having a first cylinder diameter, said first structural element, said second structural element and said third structural element defining a second cylinder support configuration for supporting another cylinder when the another cylinder is provided between said lower housing half and said upper housing half, the another cylinder having a second cylinder diameter, said second cylinder diameter being less than said first cylinder diameter, wherein at a given instance only one cylinder is arranged between said lower housing half and said upper housing half.

* * * * *